US011332425B2

(12) United States Patent
Xu et al.

(10) Patent No.: US 11,332,425 B2
(45) Date of Patent: May 17, 2022

(54) MAGNESIUM ALKOXIDE PARTICLE AND APPLICATION THEREOF (71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Xiudong Xu, Beijing (CN); Zhong Tan, Beijing (CN); Qilong Zhou, Beijing (CN); Rui Zhang, Beijing (CN); Weiwei Song, Beijing (CN); Jinhua Yu, Beijing (CN); Fengkui Li, Beijing (CN); Shanshan Yin, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 86 days.

(21) Appl. No.: 16/345,596

(22) PCT Filed: Oct. 26, 2017

(86) PCT No.: PCT/CN2017/107758
§ 371 (c)(1),
(2) Date: Apr. 26, 2019

(87) PCT Pub. No.: WO2018/077209
PCT Pub. Date: May 3, 2018

(65) Prior Publication Data
US 2019/0270690 A1 Sep. 5, 2019

(30) Foreign Application Priority Data

Oct. 26, 2016 (CN) .......................... 201610949275.9

(51) Int. Cl.
*C07C 31/30* (2006.01)
*C08F 4/02* (2006.01)
(Continued)

(52) U.S. Cl.
CPC .............. *C07C 31/30* (2013.01); *C08F 4/642* (2013.01); *C08F 4/649* (2013.01); *C08F 110/06* (2013.01);
(Continued)

(58) Field of Classification Search
CPC .......... C07C 31/30; C08F 4/02; C08F 110/06; C08F 4/6494; C08F 10/02; C07F 7/28
See application file for complete search history.

(56) References Cited

U.S. PATENT DOCUMENTS

| 4,959,336 | A | * | 9/1990 | Job | ...................... | B01J 31/0212 |
| | | | | | | 502/104 |
| 2004/0198589 | A1 | | 10/2004 | Tanase et al. | | |
| 2008/0281059 | A1 | * | 11/2008 | Tanase | ................... | C07C 31/28 |
| | | | | | | 526/123.1 |

FOREIGN PATENT DOCUMENTS

| CN | 1006071 | B | 12/1989 |
| CN | 1453298 | A | 11/2003 |

(Continued)

OTHER PUBLICATIONS

Machine translation of JP 2004-210683A. (Year: 2004).*
(Continued)

Primary Examiner — Catherine S Branch
(74) Attorney, Agent, or Firm — Novick, Kim & Lee, PLLC; Allen Xue (57) ABSTRACT The magnesium alkoxide particle contains the reaction product of the following components: 1) a magnesium powder;
(Continued)

2) a mixed alcohol; 3) a halogenating agent; and 4) a titanate compound. The magnesium alkoxide particle is used for preparing a catalyst for olefin polymerization.

25 Claims, 6 Drawing Sheets

(51) Int. Cl.
*C08F 110/06* (2006.01)
*C08F 4/649* (2006.01)
*C08F 10/02* (2006.01)
*C07F 7/28* (2006.01)
*C08F 4/642* (2006.01)
*C07C 29/70* (2006.01)
*C08F 10/06* (2006.01)
*C08F 10/08* (2006.01)

(52) U.S. Cl.
CPC .............. *C07C 29/70* (2013.01); *C08F 4/02* (2013.01); *C08F 10/02* (2013.01); *C08F 10/06* (2013.01); *C08F 10/08* (2013.01)

(56) References Cited

FOREIGN PATENT DOCUMENTS

| CN | 1946664 A | 4/2007 |
|---|---|---|
| CN | 101906017 A | 12/2010 |
| CN | 104356257 A | 2/2015 |
| CN | 104250396 B * | 8/2016 |
| JP | 2004210683 A * | 7/2004 |

OTHER PUBLICATIONS

Kahraman et al, "Polymerization of Propylene Using a Prepolymerized High-Active Ziegler-Natta Catalyst. I. Kinetic Studies," J. Appl. Poly. Sci., vol. 60, 333-342 (1996). (Year: 1996).*
Machine translation of CN 104250396B. (Year: 2016).*

* cited by examiner

MAGNESIUM ALKOXIDE PARTICLE AND APPLICATION THEREOF

CROSS-REFERENCE TO RELATED APPLICATIONS

This application is a 371 of PCT/2017/107758 filed on Oct. 26, 2017, which claims the benefit of priority of the Chinese patent application CN201610949275.9, entitled "Magnesium alkoxide particle and application thereof" and filed on Oct. 26, 2016. The entirety of the above application is incorporated herein by reference.

FIELD OF THE INVENTION

The present invention relates to the technical filed of catalyst, in particular to a magnesium alkoxide particle and application thereof.

BACKGROUND OF THE INVENTION

As people's demand for polyolefin increases, requirements for an olefin polymerization catalyst are increasingly higher. Currently, the most widely used catalyst is the Ziegler-Natta catalyst carried by magnesium chloride. In methods for preparing a catalyst disclosed in Chinese Patent CN85100997A and Chinese Patent CN1453298A, a solid catalyst component is generally made up of magnesium, titanium, halogen and an electron donating organic compound. However, it is impossible for one catalyst to meet all of various properties, such as proper particle size and shape, uniform particle distribution, particle minimization and high bulk density, as well as high catalyst activity and stereoregularity. A supported catalyst using alkoxymagnesium as a carrier can have more excellent properties.

In the preparation of the α-olefin polymerization catalyst, particle morphology of alkoxymagnesium powder faithfully reflects particle morphology of the catalyst. In an olefin polymerization process of the catalyst, bulk density of a polymer determines a size of an olefin polymerization production load, so it is of great significance to increase the bulk density of the polymer. The particle morphology and the bulk density determine fluidity of polymer powder, and fluidity of a particulate material is also very important for smooth production and transportation. Rapid outflow of alkoxymagnesium powder saves time and money especially during filling, transferring and emptying operations. Therefore, excellent particle morphology and high bulk density are important goals for the preparation of alkoxymagnesium.

SUMMARY OF THE INVENTION

Inventors of the present invention have conducted in-depth studies on direct reaction of metallic magnesium with a mixed alcohol to produce spherical microparticle alkoxymagnesium. The result shows that bulk density of alkoxymagnesium particle provided by the present invention is remarkably improved, and particle size distribution is uniform. A prepared catalyst has high polymerization activity, high polymer bulk density, good particle morphology, excellent fluidity, and less fine powder during polymerization.

The alkoxymagnesium particle comprises a reaction product of following components: 1) magnesium powder; 2) a mixed alcohol; 3) a halogenating agent; and 4) a titanate compound.

According to an embodiment of the present invention, the titanate compound has a structure as shown in Formula I:

$$(R^1O)_a Ti(OR^2)_b (OR^3)_c X_d \quad \text{Formula I,}$$

wherein, $R^1$, $R^2$ and $R^3$ may be identical to or different from each other, and are selected from a group consisting of H and alkyl, in particular $C_1$-$C_{10}$ linear or branched alkyl; X is selected from a group consisting of alkoxy, in particular $C_1$-$C_{10}$ alkoxy, carboxyl, halogen (for example, chlorine), sulfonic acid group, phosphoric acid group and sulfuric acid group; and a, b, c and d independently represent an integer number in a range of 0-4, and a+b+c+d=4. Preferably, the titanate is at least one selected from a group consisting of tetramethyl titanate, tetraethyl titanate, tetra-n-propyl titanate, tetra-n-butyl titanate, tetra-n-pentyl titanate, tetra-n-hexyl titanate, tetra-n-heptyl titanate, tetra-isooctyl titanate, tetra-n-nonyl titanate, tetra-n-decyl titanate, and isomers thereof.

According to an embodiment of the invention, the titanate compound can be used as a crosslinking agent. Without being bound by theory, the titanate compound added during the preparation of alkoxymagnesium particle may play a crosslinking role. In this way, obtained alkoxymagnesium particle can have a more compact and tighter structure, and the bulk density of the alkoxymagnesium particle can be significantly improved while good particle morphology is maintained. The alkoxymagnesium particle according to the present invention comprises a titanate compound in particle thereof. The titanate compound is distributed in the particle.

According to an embodiment of the present invention, a mass percentage of the titanate compound, in carrier particle, is 0.01-10 wt %, preferably 0.1-9 wt %, for example, 0.1-8 wt %, 0.2-8 wt %, or 0.2-7 wt %.

According to an embodiment of the invention, a dispersing agent is further comprised in the components. Preferably, the dispersing agent is an inert organic solvent at least one selected from a group consisting of hexane, heptane, octane, decane, benzene, toluene, xylene and derivatives thereof, preferably toluene. In the present invention, the inert organic solvent is used to disperse materials. The inert organic solvent can not only dilute the materials so that the materials can be better stirred, but also eliminate part of static electricity, which has a certain effect on protecting the particle morphology of a product.

According to an embodiment of the invention, a weight ratio of the titanate compound to the magnesium powder is (0.01-5):1, preferably (0.05-4):1, more preferably (0.05-3):1, and further preferably (0.05-2):1.

As to the magnesium powder used in the present invention, magnesium powder in any shape, such as particle, ribbon or powder, may be used as long as the reaction performance thereof is good. In order to ensure that the obtained alkoxymagnesium has an average particle size of 10-80 μm and has excellent particle morphology, it is required to select spherical particle of the magnesium powder having an average particle size of less than 360 μm preferably, more preferably 300-100 μm, so as to maintain a relatively uniform reaction performance.

In addition, a surface of the magnesium powder is not particularly limited. However, a reaction may be slowed if a film, such as a hydroxide, is formed on the surface of the magnesium powder. Therefore, it is preferred that magnesium powder has no film such as a hydroxide thereon.

The mixed alcohol used in the present invention is mixture of linear or branched monohydric alcohols or polyhydric alcohols. A mixture of $C_1$-$C_{10}$ alcohols is preferred. Specific examples are: methanol, ethanol, n-propanol, n-butanol, n-pentanol, n-hexanol, n-heptanol, n-octanol, n-nonanol, n-decanol, 2-propanol, 2-butanol, 2-pentanol, 2-hexanol, 2-heptanol, 2-octanol, 2-nonanol, 2-decanol, 2-ethylbutanol, 2-ethylhexanol, 4-methyl-2-pentanol, 3,3,5-trimethylpentanol, 4-methyl-3-heptanol, benzyl alcohol, 2-phenylethanol, 1-phenyl-1-propanol, ethylene glycol or glycerol.

Preferably, the mixed alcohol is a mixture of ethanol and isooctanol, in which ethanol accounts for 80-99 wt %, and isooctanol accounts for 1-20 wt %. A water content of the alcohol in the present invention is not particularly limited, and in order to obtain good performance of alkoxymagnesium, it is required that the water content is as small as possible. The water content of the alcohol is generally controlled to be less than 1000 ppm, preferably less than 200 ppm.

A molar ratio of the mixed alcohol to magnesium is (2-50):1, preferably (2.5-18):1.

According to an embodiment of the invention, the halogenating agent is an elementary halogen and/or an inorganic halide, for example, a mixture of the elementary halogen and the inorganic halide. Preferably, the halogenating agent is at least one selected from a group consisting of elementary iodine, bromine, chlorine, magnesium chloride, magnesium bromide, magnesium iodide, calcium chloride, calcium bromide, calcium iodide, mercury chloride, mercury bromide, mercury iodide and alkoxy magnesium halide. It is preferred that the halogenating agent is a mixture of at least one of elementary iodine, bromine, and chlorine, and at least one of magnesium chloride, magnesium bromide, magnesium iodide, calcium chloride, calcium bromide, calcium iodide, mercury chloride, mercury bromide, mercury iodide and alkoxy magnesium halide. More preferably, the halogenating agent is at least one selected from a group consisting of elementary iodine, magnesium iodide, magnesium chloride and alkoxy magnesium halide, and particularly preferably is a mixture of elementary iodine and magnesium chloride. Iodine or magnesium chloride may be applied to the reaction in pure form or in solution. Iodine and magnesium chloride may be separately added to a reaction system, or may be partially or completely mixed together to be added to the reaction system.

According to an embodiment of the present invention, a molar ratio of the halogenating agent to the magnesium powder measuring by halogen atoms is (0.0002-0.2):1, preferably (0.0025-0.05):1. The inventors have found that an amount of halogen atoms added affects the particle morphology and particle size of alkoxymagnesium finally obtained. When the amount of halogen atoms used is too small, obtained alkoxymagnesium has very poor particle morphology; and if the amount of halogen atoms used is too large, not only cost of preparing alkoxymagnesium increases, but also the particle size of alkoxymagnesium is nonuniform, the reaction being difficult to be controlled as well.

According to an embodiment of the present invention, a method for preparing the alkoxymagnesium particle comprises: providing a reaction system comprising 1) magnesium powder, 2) the mixed alcohol, 3) the halogenating agent, and 4) the titanate compound, and allowing the reaction system to carry out a reaction at a temperature so as to obtain the alkoxymagnesium particle. An order for adding reaction materials may be determined as needed. Specifically, a method for adding the titanate compound and the halogenating agent is not particularly limited. The titanate compound and the halogenating agent may be added by dissolving in ethanol, or may be directly added to the magnesium powder and the alcohol in a solid or liquid form, or may be dropped, during a process of heating the magnesium powder and an alcohol solution, into the alcohol solution of the halogenating agent.

All reactions of the present invention are carried out under an inert gas atmosphere, for example, under an atmosphere of argon or nitrogen, and nitrogen is preferably used in the present invention.

Further, for addition of the magnesium powder, the mixed alcohol, the halogen-containing substance, and an inert solvent, reactants may be initially fed in whole or in batch. Feeding raw materials in batch may prevent instantaneous generation of a large amount of hydrogen and prevent droplets of alcohol or halogen caused by the instantaneous generation of the large amount of hydrogen, and therefore such a feeding manner is preferred in view of safety. The number of batches divided may be determined according to a size of a reaction tank and amounts of various materials used.

A reaction temperature of the present invention may be in a range from 0° C. to a reflux temperature of the reaction system. A slight change in the reaction pressure causes a change in the reflux temperature. The higher a selected reaction temperature is, the faster the reaction proceeds. The reaction temperature may also be changed during the reaction, and the particle size and the particle morphology may be changed by selecting the reaction temperature. A preferred reaction temperature in the present invention is the reflux temperature of the reaction system.

A degree of progress of the reaction is determined by observing a discharge amount of hydrogen generated by the reaction, and the reaction time is usually 2-30 h.

According to an embodiment of the present invention, a dispersing agent is further comprised in the reaction system, and the reaction is carried out in the dispersing agent. The dispersing agent may be an inert organic solvent, preferably at least one selected from a group consisting of hexane, heptane, octane, decane, benzene, toluene, xylene, and derivatives thereof, more preferably being toluene.

According to an embodiment of the invention, a product is dried or suspended in a dispersing agent.

After the reaction, the product may be washed with an alcohol and/or a mixture of alcohols for preparing alkoxymagnesium; the product may also be washed with an organic solvent used in the reaction; in accordance with specific conditions, it may be selected that the product is not washed, and a manner of washing and a number of times thereof are not particularly limited.

According to the present invention, alkoxymagnesium particle are provided, which comprise a titanate compound in its particle. The titanate compound is distributed in the particle in an interior thereof and on a surface thereof. Without being bound by theory, the titanate compound added during the preparation of alkoxymagnesium particle may play a crosslinking role. In this way, obtained alkoxymagnesium particle can have a more compact and tighter structure, and the bulk density of the alkoxymagnesium particle can be significantly improved while good particle morphology is maintained. The alkoxymagnesium particle according to the present invention comprises a titanate compound in particle thereof. The titanate compound is distributed in the particle.

According to an embodiment of the present invention, a mass percentage of the titanate compound, in carrier particle, is 0.01-10 wt %, preferably 0.1-9 wt %, for example, 0.1-8 wt %, 0.2-8 wt %, or 0.2-7 wt %.

According to an embodiment of the present invention, the titanate compound has a structure as shown in formula I:

$$(R^1O)_a Ti(OR^2)_b (OR^3)_c X_d \quad \text{Formula I,}$$

wherein, $R^1$, $R^2$ and $R^3$ may be identical to or different from each other, and are selected from a group consisting of H and alkyl, in particular $C_1$-$C_{10}$ linear or branched alkyl; X is selected from a group consisting of alkoxy, in particular $C_1$-$C_{10}$ alkoxy, carboxyl, halogen (for example, chlorine), sulfonic acid group, phosphoric acid group and sulfuric acid group; and a, b, c and d independently represent an integer number from 0 to 4, and a+b+c+d=4. Preferably, the titanate is at least one selected from a group consisting of tetramethyl titanate, tetraethyl titanate, tetra-n-propyl titanate, tetra-n-butyl titanate, tetra-n-pentyl titanate, tetra-n-hexyl titanate, tetra-n-heptyl titanate, tetra-isooctyl titanate, tetra-n-nonyl titanate, tetra-n-decyl titanate, and isomers thereof.

According to an embodiment of the present invention, a method for preparing alkoxymagnesium particle comprises: providing a reaction system comprising 1) magnesium powder, 2) a mixed alcohol, 3) a halogenating agent, and 4) a titanate compound, the reaction system being used to carry out a reaction so as to obtain the alkoxymagnesium particle. An order for adding reaction materials may be determined as needed. Specifically, a method for adding the titanate compound and the halogenating agent is not particularly limited. The titanate compound and the halogenating agent may be added by dissolving in ethanol, or may be directly added to the magnesium powder and the alcohol in a solid or liquid form, or may be dropped, during a process of heating the magnesium powder and an alcohol solution, into the alcohol solution of the halogenating agent.

All reactions of the present invention are carried out under an inert gas atmosphere, for example, under an atmosphere of argon or nitrogen, and nitrogen is preferably used in the present invention.

Further, for addition of the magnesium powder, the mixed alcohol, the halogen-containing substance, and an inert solvent, reactants may be initially fed in whole or in batch. Feeding raw materials in batch may prevent instantaneous generation of a large amount of hydrogen and prevent droplets of alcohol or halogen caused by the instantaneous generation of the large amount of hydrogen, and therefore such a feeding manner is preferred in view of safety. The number of batches divided may be determined according to a size of a reaction tank and amounts of various materials used.

A reaction temperature of the present invention may be 0° C. to a reflux temperature of the reaction system. A slight change in the reaction pressure causes a change in the reflux temperature. The higher a selected reaction temperature is, the faster the reaction proceeds. The reaction temperature may also be changed during the reaction, and the particle size and the particle morphology may be changed by selecting the reaction temperature. A preferred reaction temperature in the present invention is the reflux temperature of the reaction system.

A degree of progress of the reaction is determined by observing a discharge amount of hydrogen generated by the reaction, and the reaction time is usually 2 to 30 hours.

According to an embodiment of the invention, a weight ratio of the titanate compound to the magnesium powder is (0.01-5):1, preferably (0.05-4):1, more preferably (0.05-3):1, and further preferably (0.05-2):1.

As to the magnesium powder used in the present invention, magnesium powder in any shape may be used if reaction performance thereof is good. For example, magnesium powder in a shape of particle, magnesium powder in a shape of ribbon or magnesium powder in a shape of powder may all be used. In order to ensure that the obtained alkoxymagnesium has an average particle size of 10-80 μm and has excellent particle morphology, it is required to select spherical particle of the magnesium powder having an average particle size of less than 360 μm preferably, more preferably 300-100 μm, so as to maintain a relatively uniform reaction performance.

In addition, a surface of the magnesium powder is not particularly limited. However, a reaction may be slowed if a film, such as a hydroxide, is formed on the surface of the magnesium powder. Therefore, it is preferred that magnesium powder has no film such as a hydroxide thereon.

The mixed alcohol used in the present invention is a linear or branched monohydric alcohol or polyhydric alcohol. A mixture of $C_1$-$C_{10}$ alcohols is preferred. Specific examples are: methanol, ethanol, n-propanol, n-butanol, n-pentanol, n-hexanol, n-heptanol, n-octanol, n-nonanol, n-decanol, 2-propanol, 2-butanol, 2-pentanol, 2-hexanol, 2-heptanol, 2-octanol, 2-nonanol, 2-decanol, 2-ethylbutanol, 2-ethylhexanol, 4-methyl-2-pentanol, 3,3,5-trimethylpentanol, 4-methyl-3-heptanol, benzyl alcohol, 2-phenylethanol, 1-phenyl-1-propanol, ethylene glycol or glycerol.

Preferably, the mixed alcohol is a mixture of ethanol and isooctanol, in which ethanol accounts for 80-99 wt %, and isooctanol accounts for 1-20 wt %. A water content of the alcohol in the present invention is not particularly limited, and in order to obtain good performance of alkoxymagnesium, it is required that the water content is as small as possible. The water content of the alcohol is generally controlled to be less than 1000 ppm, preferably less than 200 ppm.

A molar ratio of the mixed alcohol to magnesium is (2-50):1, preferably (2.5-18):1.

According to an embodiment of the invention, the halogenating agent is an elementary halogen and/or an inorganic halide, for example, a mixture of the elementary halogen and the inorganic halide. Preferably, the halogenating agent is selected from a group consisting of elementary iodine, bromine, chlorine, magnesium chloride, magnesium bromide, magnesium iodide, calcium chloride, calcium bromide, calcium iodide, mercury chloride, mercury bromide, mercury iodide and alkoxy magnesium halide. It is preferred that the halogenating agent is a mixture of at least one of elementary iodine, bromine, and chlorine and at least one of magnesium chloride, magnesium bromide, magnesium iodide, calcium chloride, calcium bromide, calcium iodide, mercury chloride, mercury bromide, mercury iodide and alkoxy magnesium halide. More preferably, the halogenating agent is at least one selected from a group consisting of elementary iodine, magnesium iodide, magnesium chloride and alkoxy magnesium halide, and particularly preferably is a mixture of elementary iodine and magnesium chloride. Iodine or magnesium chloride may be applied to the reaction in pure form or in solution. Iodine and magnesium chloride may be separately added to a reaction system, or may be partially or completely mixed together to be added to the reaction system.

According to an embodiment of the present invention, a molar ratio of the halogenating agent to the magnesium powder measuring by halogen atoms is (0.0002-0.2):1, preferably (0.0025-0.05):1. The inventors have found that an amount of halogen atoms added affects the particle morphology and particle size of alkoxymagnesium finally obtained. When the amount of halogen atoms used is too small, obtained alkoxymagnesium has very poor particle morphology; and if the amount of halogen atoms used is too large, not only cost of preparing alkoxymagnesium increases, but also the particle size of alkoxymagnesium is nonuniform, the reaction being difficult to be controlled as well.

According to an embodiment of the present invention, a dispersing agent is further comprised in the reaction system, and the reaction is carried out in the dispersing agent. The dispersing agent may be an inert organic solvent, preferably at least one selected from a group consisting of hexane, heptane, octane, decane, benzene, toluene, xylene, and derivatives thereof, more preferably being toluene.

According to an embodiment of the invention, a product is dried or suspended in a dispersing agent.

After the reaction, the product may be washed with an alcohol and/or a mixture of alcohols for preparing alkoxymagnesium; the product may also be washed with an organic solvent used in the reaction; in accordance with specific conditions, it may be selected that the product is not washed, and a manner of washing and a number of times thereof are not particularly limited.

Another objective of the present invention is to provide a Ziegler-Natta catalyst component, comprising a reaction product of the following components:

A) aforementioned alkoxymagnesium particle;

B) a titanium-containing halide; and

C) an electron donor compound.

According to an embodiment of the invention, the electron donor compound is at least one selected from a group consisting of a carboxylate compound, a 2,3-di-non-linear alkyl-2-cyano disuccinate electron donor compound, and an aliphatic ether compound. The electron donor compound may be used separately, or a combination of several electron donor compounds may be used. An amount of the electron donor compound used is 0.005-10 mol relative to an amount of magnesium in 1 mol of a dialkoxymagnesium compound.

A carboxylate electron donor compound is selected from a group consisting of a mono benzoate compound or a phthalate compound as shown in Formula II Formula II wherein, $R_1$ and $R_2$ are independently selected from a group consisting of substituted or unsubstituted $C_1$-$C_8$ alkyl, $C_3$-$C_{10}$ cycloalkyl or $C_6$-$C_{20}$ aryl; $R_3$-$R_6$ are independently selected from a group consisting of hydrogen, halogen, $C_1$-$C_4$ alkyl or $C_1$-$C_4$ alkoxy, wherein, preferably, at least three of $R_3$-$R_6$ are hydrogen, and more preferably, the carboxylate electron donor compound is at least one selected from a group consisting of di-n-butyl phthalate, diisobutyl phthalate, diethyl phthalate, dipentyl phthalate, dioctyl phthalate, methyl benzoate, ethyl benzoate, propyl benzoate, isopropyl benzoate, butyl benzoate and isobutyl benzoate.

A 2,3-di-non-linear alkyl-2-cyano disuccinate compound has a structure as shown in Formula III:

Formula III wherein, $R_1$ and $R_2$ may be the identical to or different from each other, and represent linear alkane of 1 to 10 carbon atoms, branched alkyl or cycloalkyl of 3 to 10 carbon atoms, aryl of 6 to 10 carbon atoms, alkaryl or aralkyl of 7 to 10 carbon atoms, wherein a hydrogen atom on a carbon in said alkyl, cycloalkyl, aryl, alkaryl or aralkyl may be optionally substituted by a halogen (hetero) atom, alkyl or alkoxy, and a carbon atom on a main chain may be optionally substituted by a hetero atom. $R_1$ and $R_2$ groups are preferably selected from a group consisting of linear alkyl of 1 to 8 carbon atoms, branched alkyl or cycloalkyl of 3 to 8 carbon atoms, and aryl of 6 to 10 carbon atoms. More preferably, $R_1$ and $R_2$ groups are linear or branched alkyl of 1 to 6 carbon atoms, in particular methyl, ethyl, n-propyl, isopropyl, n-butyl, isobutyl, tert-butyl, n-pentyl, isopentyl, tert-pentyl, cyclopentyl, cyclohexyl or phenyl. The 2,3-di-non-linear alkyl-2-cyano disuccinate compound is selected from a suitable compound, examples of which including, but not limited to:

diethyl 2-cyano-2,3-di-n-propyl succinate, diethyl 2-cyano-2,3-diisopropyl succinate, diethyl 2-cyano-2,3-di-n-butyl succinate, diethyl 2-cyano-2,3-diisobutyl succinate, diethyl 2-cyano-2,3-di-n-pentyl succinate, diethyl 2-cyano-2,3-diisopentyl succinate, diethyl 2-cyano-2,3-dicyclopentyl succinate, diethyl 2-cyano-2,3-di-n-hexyl succinate, diethyl 2-cyano-2,3-diisohexyl succinate;

diethyl 2-cyano-2-isopropyl-3-n-propyl succinate, diethyl 2-cyano-2-isopropyl-3-n-butyl succinate, diethyl 2-cyano-2-isopropyl-3-isobutyl succinate, diethyl 2-cyano-2-isopropyl-3-n-pentyl succinate, diethyl 2-cyano-2-isopropyl-3-isopentyl succinate, diethyl 2-cyano-2-isopropyl-3-cyclopentyl succinate;

diethyl 2-cyano-2-n-butyl-3-n-propyl succinate, diethyl 2-cyano-2-n-butyl-3-isopropyl succinate, diethyl 2-cyano-2-n-butyl-3-isobutyl succinate, diethyl 2-cyano-2-n-butyl-3-n-pentyl succinate, diethyl 2-cyano-2-n-butyl-3-isopentyl succinate, diethyl 2-cyano-2-n-butyl-3-cyclopentyl succinate;

diethyl 2-cyano-2-isobutyl-3-n-propyl succinate, diethyl 2-cyano-2-isobutyl-3-isopropyl succinate, diethyl 2-cyano-2-isobutyl-3-n-butyl succinate, diethyl 2-cyano-2-isobutyl-3-n-pentyl succinate, diethyl 2-cyano-2-isobutyl-3-isopentyl succinate, diethyl 2-cyano-2-isobutyl-3-cyclopentyl succinate;

diethyl 2-cyano-2-n-pentyl-3-n-propyl succinate, diethyl 2-cyano-2-n-pentyl-3-isopropyl succinate, diethyl 2-cyano-2-n-pentyl-3-n-butyl succinate, diethyl 2-cyano-2-n-pentyl-3-isobutyl succinate, diethyl 2-cyano-2-n-pentyl-3-isopentyl succinate, diethyl 2-cyano-2-n-pentyl-3-cyclopentyl succinate;

diethyl 2-cyano-2-isopentyl-3-n-propyl succinate, diethyl 2-cyano-2-isopentyl-3-isopropyl succinate, diethyl 2-cyano-2-isopentyl-3-n-butyl succinate, diethyl 2-cyano-2-isopentyl-3-isobutyl succinate, diethyl 2-cyano-2-isopentyl-3-n-pentyl succinate, diethyl 2-cyano-2-isopentyl-3-cyclopentyl succinate;

diethyl 2-cyano-2-cyclopentyl-3-n-propyl succinate, diethyl 2-cyano-2-cyclopentyl-3-isopropyl succinate, diethyl 2-cyano-2-cyclopentyl-3-n-butyl succinate, diethyl 2-cyano-2-cyclopentyl-3-isobutyl succinate, diethyl 2-cyano-2-cyclopentyl-3-n-pentyl succinate, diethyl 2-cyano-2-cyclopentyl-3-isopentyl succinate;

preferably selected from a group consisting of diethyl 2-cyano-2,3-diisopropyl succinate, diethyl 2-cyano-2,3-di-n-butyl succinate, diethyl 2-cyano-2,3-diisobutyl succinate, diethyl 2-cyano-2,3-di-n-pentyl succinate, diethyl 2-cyano-2,3-diisopentyl succinate;

diethyl 2-cyano-2-isopropyl-3-n-propyl succinate, diethyl 2-cyano-2-isopropyl-3-n-butyl succinate, diethyl 2-cyano-2-isopropyl-3-isobutyl succinate, diethyl 2-cyano-2-isopropyl-3-n-pentyl succinate, diethyl 2-cyano-2-isopropyl-3-isopentyl succinate, diethyl 2-cyano-2-isopropyl-3-cyclopentyl succinate;

diethyl 2-cyano-2-n-butyl-3-isopropyl succinate, diethyl 2-cyano-2-n-butyl-3-isobutyl succinate, diethyl 2-cyano-2-n-butyl-3-n-pentyl succinate;

diethyl 2-cyano-2-isobutyl-3-isopropyl succinate, diethyl 2-cyano-2-isobutyl-3-n-butyl succinate, diethyl 2-cyano-2-isobutyl-3-n-pentyl succinate;

diethyl 2-cyano-2-n-pentyl-3-isopropyl succinate, diethyl 2-cyano-2-n-pentyl-3-n-butyl succinate, diethyl 2-cyano-2-n-pentyl-3-isobutyl succinate;

diethyl 2-cyano-2-isopentyl-3-isopropyl succinate, diethyl 2-cyano-2-isopentyl-3-n-butyl succinate, diethyl 2-cyano-2-isopentyl-3-isobutyl succinate;

diethyl 2-cyano-2-cyclopentyl-3-isopropyl succinate, diethyl 2-cyano-2-cyclopentyl-3-n-butyl succinate, diethyl 2-cyano-2-cyclopentyl-3-isobutyl succinate; and most preferably selected from a group consisting of diethyl 2-cyano-2,3-diisopropyl succinate, diethyl 2-cyano-2,3-di-n-butyl succinate, diethyl 2-cyano-2,3-diisobutyl succinate, diethyl 2-cyano-2,3-di-n-pentyl succinate, diethyl 2-cyano-2,3-diisopentyl succinate;

diethyl 2-cyano-2-isopropyl-3-n-butyl succinate, diethyl 2-cyano-2-isopropyl-3-isobutyl succinate, diethyl 2-cyano-2-isopropyl-3-n-pentyl succinate, diethyl 2-cyano-2-isopropyl-3-isopentyl succinate, diethyl 2-cyano-2-isopropyl-3-cyclopentyl succinate;

diethyl 2-cyano-2-n-butyl-3-isopropyl succinate, diethyl 2-cyano-2-isobutyl-3-isopropyl succinate, diethyl 2-cyano-2-n-pentyl-3-isopropyl succinate, diethyl 2-cyano-2-isopentyl-3-isopropyl succinate, and diethyl 2-cyano-2-cyclopentyl-3-isopropyl succinate.

The 2,3-di-non-linear alkyl-2-cyano disuccinate compound may be used independently or in combination, and an amount thereof used is 0.005-10 mol relative to an amount of magnesium in 1 mol of a spherical dialkoxymagnesium compound.

Examples of the aliphatic ether compound include, but not limited to, at least one of: 2,2'-di-n-propyl-1,3-dimethyl ether, 2,2'-diisopropyl-1,3-dimethyl ether, 2,2'-di-n-butyl-1,3-dimethyl ether, 2,2'-diisobutyl-1,3-dimethyl ether, 2,2'-di-n-pentyl-1,3-dimethyl ether, 2,2'-diisopentyl-1,3-dimethyl ether, 2,2'-di-n-hexyl-1,3-dimethyl ether, 2,2'-diisohexyl-1,3-diether, 2-n-propyl-2-isopropyl-1,3-dimethyl ether, 2-n-propyl-2-n-butyl-1,3-dimethyl ether, 2-n-propyl-2-isobutyl-1,3-dimethyl ether, 2-n-propyl-2-n-pentyl-1,3-dimethyl ether, 2-n-propyl-2-isopentyl-1,3-dimethyl ether, 2-n-propyl-2-n-hexyl-1,3-dimethyl ether, 2-n-propyl-2-isohexyl-1,3-dimethyl ether, 2-isopropyl-2-n-butyl-1,3-dimethyl ether, 2-isopropyl-2-isobutyl-1,3-dimethyl ether, 2-isopropyl-2-n-pentyl-1,3-dimethyl ether, 2-isopropyl-2-isopentyl-1,3-dimethyl ether, 2-isopropyl-2-n-hexyl-1,3-dimethyl ether, 2-iso-propyl-2-isohexyl-1,3-dimethyl ether, 2-n-butyl-2-isobutyl-1,3-dimethyl ether, 2-n-butyl-2-n-pentyl-1,3-dimethyl ether, 2-n-butyl-2-isopentyl-1,3-dimethyl ether, 2-n-butyl-2-n-hexyl-1,3-dimethyl ether, 2-n-butyl-2-isohexyl-1,3-dimethyl ether, 2-isobutyl-2-n-pentyl-1,3-dimethyl ether, 2-isobutyl-2-isopentyl-1,3-dimethyl ether, 2-isobutyl-2-n-hexyl-1,3-dimethyl ether, 2-isobutyl-2-isohexyl-1,3-dimethyl ether, 2-n-pentyl-2-isopentyl-1,3-dimethyl ether, 2-n-pentyl-2-n-hexyl-1,3-dimethyl ether, 2-n-pentyl-2-isohexyl-1,3-dimethyl ether, 2-isopentyl-2-n-hexyl-1,3-dimethyl ether, 2-isopentyl-2-isohexyl-1,3-dimethyl ether and 2-n-hexyl-2-isohexyl-1,3-dimethyl ether; preferably at least one selected from a group consisting of: 2-isopropyl-2-(3-methyl butyl)-1,3-dimethoxy propane, 2,2'-diisopropyl-1,3-dimethyl ether, 2,2'-di-n-butyl-1,3-dimethyl ether, 2,2'-diisobutyl-1,3-dimethyl ether, 2,2'-di-n-pentyl-1,3-dimethyl ether, 2,2'-diisopentyl-1,3-dimethyl ether, 2-n-propyl-2-isopropyl-1,3-dimethyl ether, 2-n-propyl-2-isobutyl-1,3-dimethyl ether, 2-n-propyl-2-isopentyl-1,3-dimethyl ether, 2-isopropyl-2-n-butyl-1,3-dimethyl ether, 2-isopropyl-2-isobutyl-1,3-dimethyl ether, 2-isopropyl-2-n-pentyl-1,3-dimethyl ether, 2-isopropyl-2-isopentyl-1,3-dimethyl ether, 2-isopropyl-2-isohexyl-1,3-dimethyl ether, 2-n-butyl-2-isobutyl-1,3-dimethyl ether, 2-n-butyl-2-isopentyl-1,3-dimethyl ether, 2-n-butyl-2-isohexyl-1,3-dimethyl ether, 2-isobutyl-2-n-pentyl-1,3-dimethyl ether, 2-isobutyl-2-isopentyl-1,3-dimethyl ether, 2-isobutyl-2-n-hexyl-1,3-dimethyl ether, 2-isobutyl-2-isohexyl-1,3-dimethyl ether and 2-n-pentyl-2-isopentyl-1,3-dimethyl ether; and most preferably at least one selected from a group consisting of: 2-isopropyl-2-(3-methyl butyl)-1,3-dimethoxy propane, 2,2'-diisopropyl-1,3-dimethyl ether, 2,2'-diisobutyl-1,3-dimethyl ether, 2,2'-diisopentyl-1,3-dimethyl ether, 2-isopropyl-2-isobutyl-1,3-dimethyl ether, 2-isopropyl-2-n-pentyl-1,3-dimethyl ether, 2-isopropyl-2-isopentyl-1,3-dimethyl ether, 2-isopropyl-2-isohexyl-1,3-dimethyl ether, 2-isobutyl-2-n-pentyl-1,3-dimethyl ether, 2-isobutyl-2-isopentyl-1,3-dimethyl ether and 2-n-pentyl-2-isopentyl-1,3-dimethyl ether. An amount of the aliphatic ether compound used is 0.005-10 mol relative to the amount of magnesium in 1 mol of the spherical dialkoxymagnesium compound.

According to an embodiment of the invention, the titanium-containing halide is shown in formula IV:

$$TiX_n(OR_7)_{4-n} \quad \text{Formula IV}$$

wherein, X is halogen; $R_7$ is $C_1$-$C_{20}$ alkyl; and n is an integer number in a range of 0-4.

According to an embodiment of the invention, an amount of the titanium-containing halide used is 0.5-100 mol relative to the amount of magnesium in 1 mol of the spherical dialkoxymagnesium compound, more preferably 1-50 mol. That is, a molar ratio of the titanium-containing halide to the alkoxymagnesium particle is preferably (0.5-100):1, more preferably (1-50):1.

According to an embodiment of the present invention, when the catalyst component is prepared, a reaction temperature is in a range of –40-200° C., preferably in a range of –20-150° C., and a reaction time is in a range of 1 min to 20 h, preferably in a range of 5 min to 8 h.

A further objective of the present invention is to provide a catalyst for olefin polymerization, comprising a reaction product of the following components:

(1) the aforementioned catalyst component;
(2) an organic aluminum compound; and
(3) optionally, an external electron donor compound.

According to an embodiment of the invention, the organic aluminum compound is an organic aluminum compound shown in Formula AlR'$_m$X'$_{3-m}$, wherein R' is at least one selected from a group consisting of hydrogen, $C_1$-$C_{20}$ alkyl and $C_6$-$C_{20}$ aryl; X' is halogen; and m is an integer number in a range of 1-3.

According to an embodiment of the invention, the external electron donor compound is an organic silicon compound as shown in $R^4_p R^5_q Si(OR^6)_{4-p-q}$, wherein $R^4$ and $R^5$ are independently at least one selected from a group consisting of a halogen atom, a hydrogen atom, $C_1$-$C_{20}$ alkyl, $C_3$-$C_{20}$ cycloalkyl, $C_6$-$C_{20}$ aryl, and $C_1$-$C_{20}$ haloalkyl; $R^6$ is any one selected from a group consisting of $C_1$-$C_{20}$ alkyl, $C_3$-$C_{20}$ cycloalkyl, $C_6$-$C_{20}$ aryl, and $C_1$-$C_{20}$ haloalkyl; and p and q respectively are an integer number in a range of 0-3, and p+q<4.

According to an embodiment of the invention, a molar ratio of aluminum in the organic aluminum compound to titanium in the catalyst component is (5-5000):1, preferably (20-1000):1, and more preferably (50-500):1; and a molar ratio of aluminum in the organic aluminum compound to the external electron donor compound is (0.1-500):1, preferably (1-300):1, and most preferably (3-100):1.

The present invention further provides a method of olefin polymerization, comprising contacting olefin with the catalyst under olefin polymerization conditions. At least one of the olefin is represented by a general formula $CH_2$=CHR, in which R is any one of hydrogen and $C_1$-$C_6$ alkyl.

The method of olefin polymerization of the present invention can be used for homopolymerization of an olefin, and can also be used for copolymerization of various olefins. Specific examples of α-olefin represented by the general formula $CH_2$=CHR are ethylene, propylene, 1-n-butene, 1-n-pentene, 1-n-hexene, 1-n-octene and 4-methyl-1-pentene. More preferably, the olefin represented by the general formula $CH_2$=CHR is at least one selected from a group consisting of ethylene, propylene and 1-butene.

According to an embodiment of the invention, the olefin polymerization conditions are: a temperature of 0-150° C., preferably 60-130° C.; a time of 0.1-5 h, preferably 0.5-4 h; and a pressure of 0.01-10 MPa, preferably 0.5-5 MPa.

The present invention has the following beneficial effects.

In the present invention, a small amount of a mixture of halogen-containing substances is used as a halogenating agent. When a titanate compound and/or an inert organic solvent are/is added during the reaction, the reaction can be controlled more easily, and the particle morphology can be kept better.

Without being bound by theory, the titanate compound added during the preparation of alkoxymagnesium particle may play a crosslinking role. In this way, obtained alkoxymagnesium particle can have a more compact and tighter structure, and the bulk density of the alkoxymagnesium particle can be significantly improved while good particle morphology is maintained. Moreover, bulk density of a polymer can be improved evidently. Besides, the catalyst has good activity, and particle of the polymer have better morphology. The alkoxymagnesium particle prepared by the present invention can be used for preparation of an olefin polymerization catalyst in particular. An obtained catalyst has high activity, good particle morphology and uniform distribution, and can be used in an apparatus for producing olefin using a gas phase process. An obtained polymer has evidently improved bulk density and good fluidity, which is beneficial for long-term stable use of the catalyst.

DETAILED DESCRIPTION OF THE EMBODIMENTS

The present invention will be described in a detailed way below based on embodiments and the accompanying drawings, but the present invention is not limited by the following embodiments.

It should be noted that, evaluation of alkoxymagnesium particle and polyolefin prepared in embodiments of the present invention is made by the following methods.

1. A content of titanate in the alkoxymagnesium particle and a content of titanium atoms in an olefin polymerization catalyst component are tested with a 721 spectrophotometer.

2. A melt index (MI) of a polymer is measured with a XRZ-00 melt indexer by using a method stipulated in GB/T3682-2000.

3. A particle size and a particle distribution of dialkoxymagnesium and that of a catalyst are measured by using Malvern Mastersizer TM2000 laser diffraction method with n-hexane as a dispersant, wherein SPAN=(D90−D10)/D50.

4. A content of carboxylate electron donor in an olefin polymerization catalyst component is measured by using a gas chromatography.

5. An isotactic index (II) of the polymer is measured by the following process: 2 g of a dry polymer sample is placed in an extracter and extracted with boiling heptane for 6 h, and then a residue is dried to constant weight. Isotacticity is calculated by the following formula:

$$\text{Isotacticity II} = \text{mass of the polymer after extraction}/2 \times 100\%.$$

6. A bulk density (BD) of alkoxymagnesium and that of the polymer are measured by a method of the weight of loose solid in each unit volume.

7. A content (%) of fine powder in the polymer is obtained by sieving the polymer obtained with an 80 mesh sieve, and is a weight percentage of small size powder sieved out in the total polymer.

8. A scanning electron microscopy—energy spectrum analysis is tested by a Hitachi S-480 cold field emission scanning electron microscope, and testing is performed under a condition that a voltage of the scanning electron microscope is 1 kV.

A TEAM Octane Super energy disperse spectroscopy is used for the testing, and conditions of the testing are: a voltage of 20 KV, an amplification factor of 5000, a take-off angle of 30, a live time of 100 (s), a time constant of an amplifier of 7.68 (μs), and a resolution ratio of 128.2 (eV).

Figure 1:
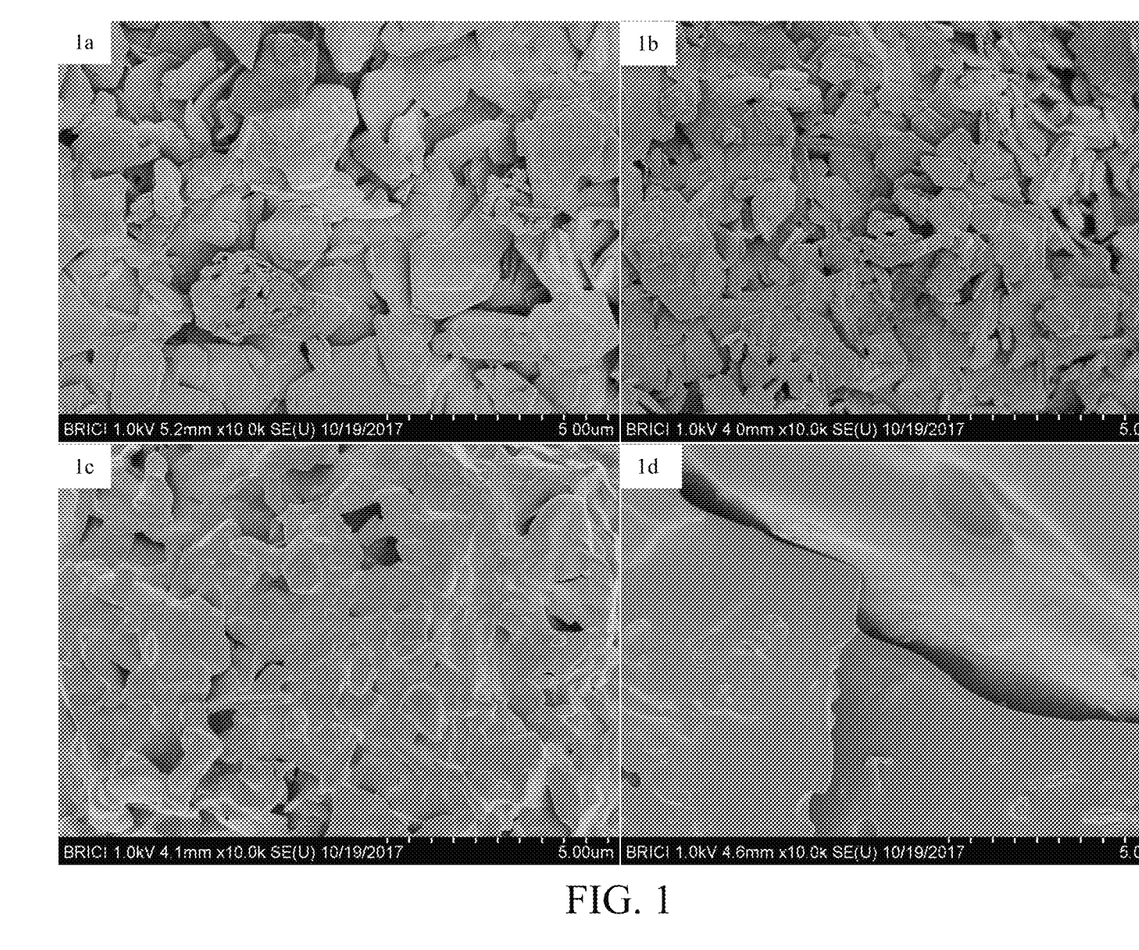
FIG. 1 shows a scanning electron microscope photograph of a cross section of alkoxymagnesium particle in a comparative example and an example according to the present invention.

FIG. 1 shows a scanning electron microscope photograph of a cross section of alkoxymagnesium particle in an example and a comparative example according to the present invention, wherein 1a, 1b, 1c and 1d correspond to Comparative Example 1, Example 2, Example 1, and Example 14, respectively. It can be seen from photographs that in the preparation of alkoxymagnesium particle, when a titanate compound is not added, obtained alkoxymagnesium is formed by a combination of polygonal flaky crystals (see 1a in FIG. 1), and after the titanate compound is added, it plays a similar role of cross-linking, so that a structure of the particle is more compact and tighter, some of the flaky crystals being combined by a certain chemical action (see FIGS. 1b, 1c and 1d) and the structure being changed.

Figure 2:
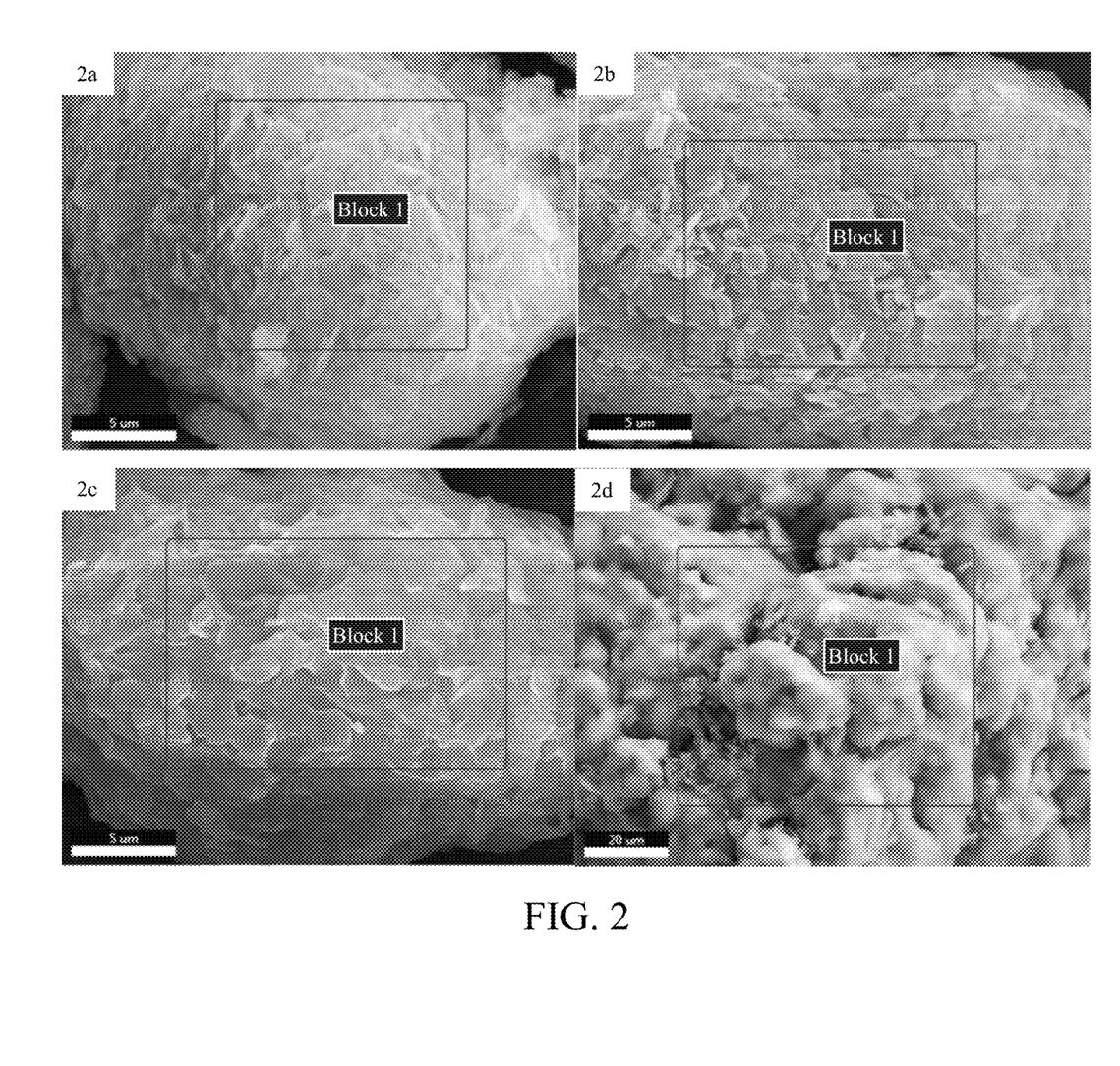
FIG. 2 shows a scanning electron microscope photograph of morphology of alkoxymagnesium particle in a comparative example and an example according to the present invention.
Figure 3A:
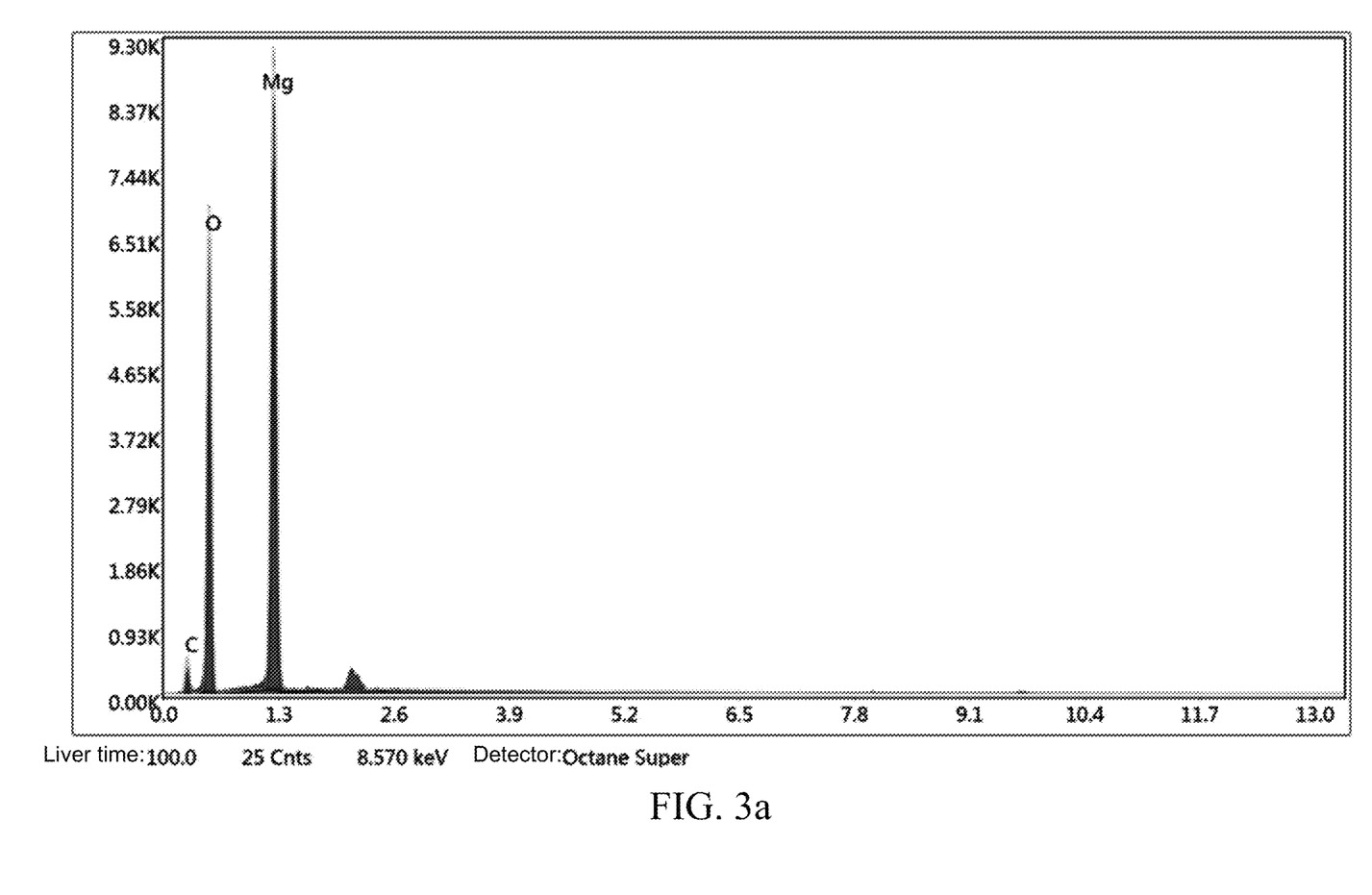
FIG. 3a shows a result of an energy spectrum analysis of Comparative Example 1 according to the present invention.
Figure 3B:
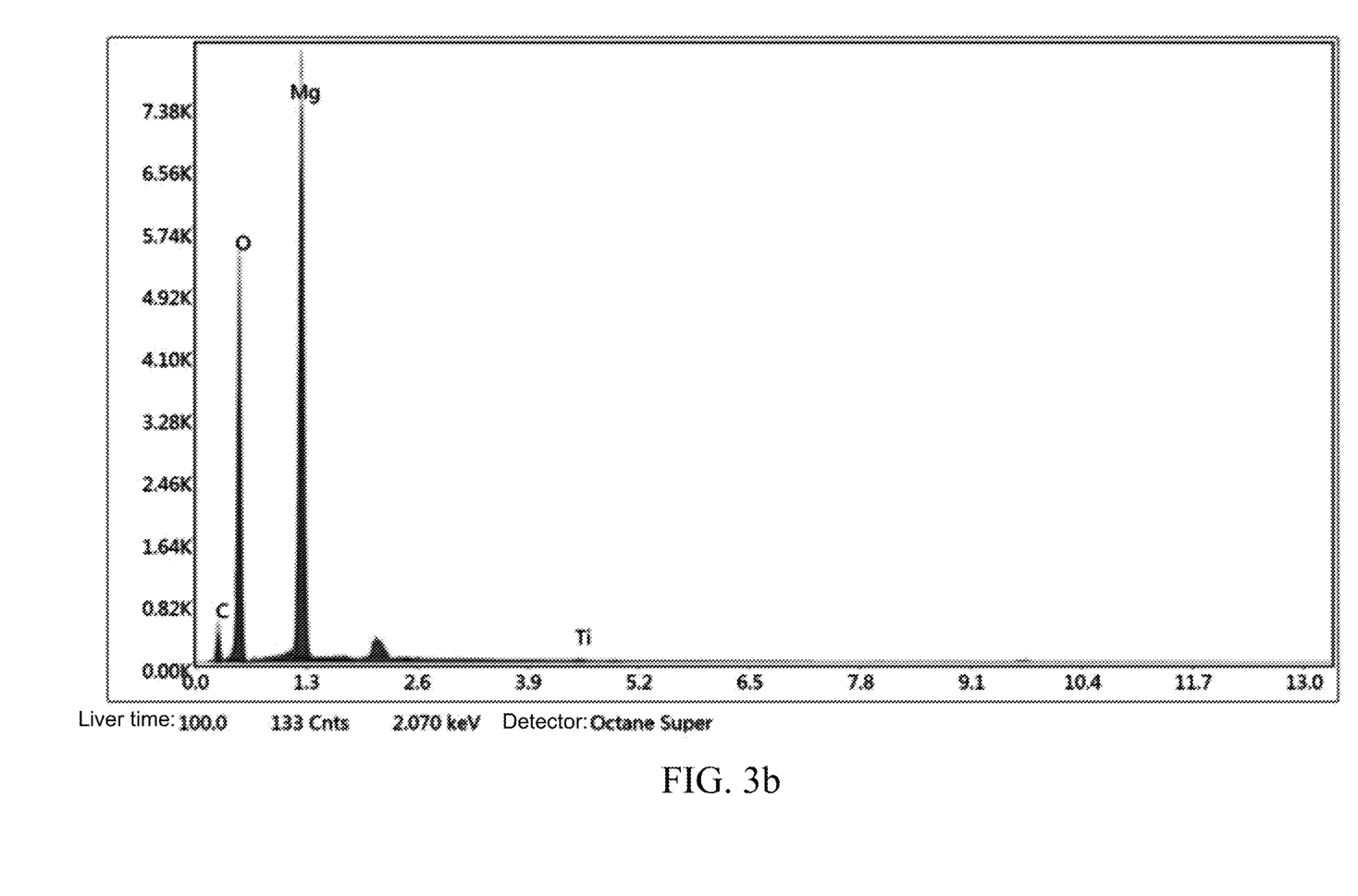
FIG. 3b shows a result of an energy spectrum analysis of Example 1 according to the present invention.
Figure 3C:
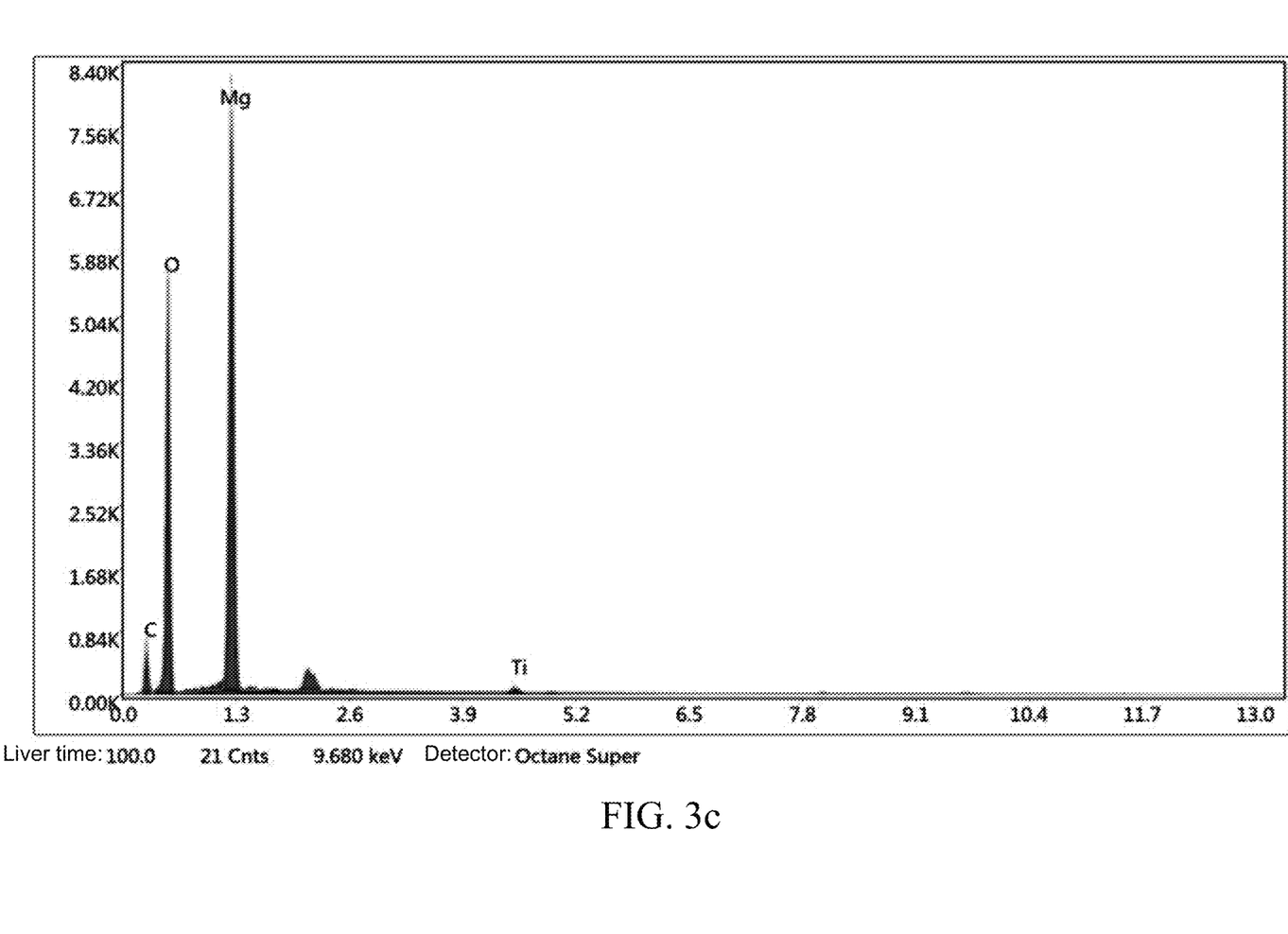
FIG. 3c shows a result of an energy spectrum analysis according to Example 2 of the present invention.
Figure 3D:
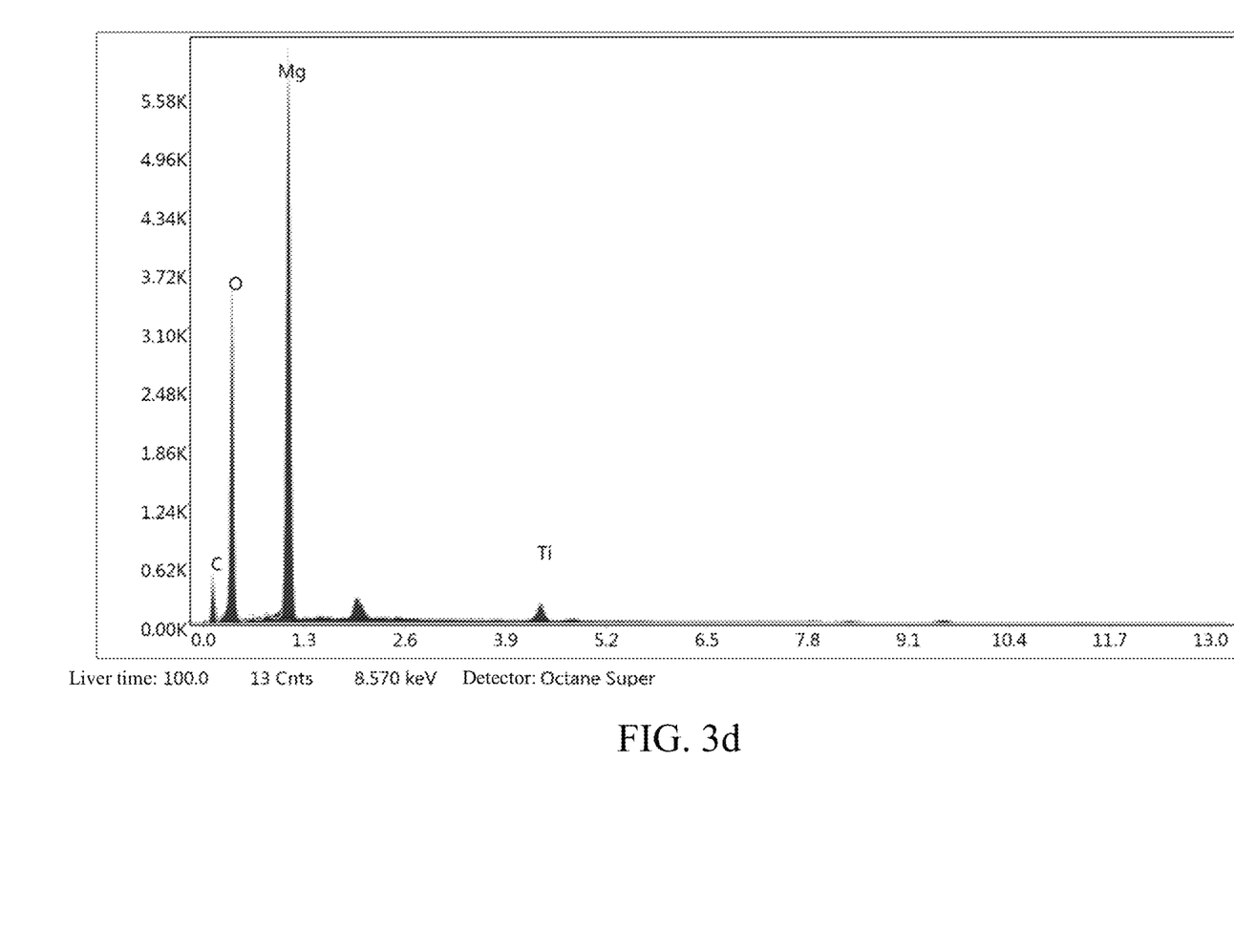
FIG. 3d shows a result of an energy spectrum analysis according to Example 14 of the present invention.

FIG. 2 shows a scanning electron microscope photograph of morphology of alkoxymagnesium particle in an example and a comparative example according to the present invention, wherein 2a, 2b, 2c and 2d correspond to Comparative Example 1, Example 2, Example 1, and Example 14, respectively. It can be seen from FIG. 2 that in the preparation of alkoxymagnesium particle, after the titanate compound is added, a structure of the particle is more compact and tighter, flaky crystals are crosslinked gradually so as to form a compact structure. Moreover, as an amount of the titanate compound added increases, the flaky crystals will not be identified finally and form a stable structural body by crosslinking. Besides, after the titanate compound is crosslinked with one particle, a plurality of particles will be crosslinked if the titanate compound is sufficient so as to form a bigger compact structure.

FIG. 3a, FIG. 3b, FIG. 3c and FIG. 3d correspond to an energy spectrum image of Comparative Example 1, Example 2, Example 1, and Example 14, respectively. By characterizing energy spectrum of selected regions in the blocks in FIG. 2, it can be seen that the alkoxymagnesium particle of the examples has titanium element therein, which shows that the titanate compound is contained in the alkoxymagnesium particle (including the interior) of the examples.

Examples 1-14

Preparation of alkoxymagnesium particle: A reactor with a stirrer was equipped with a reflux condenser, a thermometer and a burette. After air in the reactor was fully replaced with nitrogen, ethanol having a water content of less than 200 ppm and a small amount of isooctanol having a water content of less than 200 ppm were added into the reactor, and elementary iodine and magnesium chloride were also added to be dissolved. Magnesium powder (less than 300 μm) and toluene were then added. A certain amount of the titanate compound was added to a feed liquid of a reaction to carry out the reaction. After stirring, a temperature was increased to reach a reflux temperature of the reaction system. The reaction was carried out until the reaction was completed, i.e. no hydrogen was discharged. Then, washing, separating and drying were performed. Additions of respective raw materials and a result are shown in Table 1.

Preparation of a solid catalyst component by using the alkoxymagnesium particle prepared: 10 mL of toluene and 90 mL of titanium tetrachloride were added into a 300 mL reactor after air therein was repeatedly replaced with high purity nitrogen. After a temperature is increased to 50° C., a suspension prepared with 10 g of the akoxymagnesium particle prepared, 50 mL of toluene, and 1.2 mL of an electron donor compound, i.e., di-n-butyl phthalate (abbreviated as "DNBP" in Table 1), or diethyl 2,3-diisopropyl-2-dicyano succinate (abbreviated as "JS" in the Table 1), or 2-isopropyl-2-(3-methyl butyl)-1,3-dimethoxy propane (abbreviated as "2# ether" in Table 1), was added. The temperature was slowly increased up to 115° C. and maintained for 2 h, and then liquid was removed by filtration under reduced pressure. Then a mixed solution of 30 mL of titanium tetrachloride and 120 mL of toluene was added. After the temperature was increased to 110° C., 1.5 mL of the electron donor compound, i.e., di-n-butyl phthalate (abbreviated as "DNBP" in Table 1), or diethyl 2,3-diisopropyl-2-dicyano succinate (abbreviated as "JS" in Table 1), or 2-isopropyl-2-(3-methyl butyl)-1,3-dimethoxy propane (abbreviated as "2# ether" in Table 1) was added. After a stirring treatment is performed for 1 h, the liquid was removed by filtration under reduced pressure. Then, a mixed solution of 30 mL of titanium tetrachloride and 120 mL of toluene was added. The temperature was increased to 110° C., and a stirring treatment was performed for 1 h. Such treatment was repeated for 2 times, and the liquid was removed by filtration. An obtained solid was washed with 150 mL of hexane for 4 times at a temperature of 60° C., and the liquid was removed by filtration. After drying was performed, solid powder was obtained, which is the solid catalyst component. Specific data are shown in Table 1.

Propylene polymerization: In a 5 L autoclave, nitrogen gas flow was used for purging for 1 h at a temperature of 70° C., and then 5 mL of a hexane solution of triethyl aluminium (a concentration of triethyl aluminium is 0.5 mmol/ml), 1 mL of a hexane solution of cyclohexyl methyl dimethoxy silane (CHMMS) (a concentration of CHMMS is 0.10 mmol/ml), 10 mL of anhydrous hexane and 10 mg of the solid catalyst component were introduced in the nitrogen gas stream at room temperature. After the autoclave was closed, 1 L of hydrogen (in the standard state) and 2.0 L of liquid propylene were introduced. Then the temperature was increased to 70° C. in 10 min under stirring. After a polymerization was carried out at 70° C. for 2 h, the stirring was stopped. Unpolymerized propylene monomers were removed, and polymers were collected for testing. Specific data are shown in Table 1.

Comparative Examples 1-2

Preparation of an alkoxymagnesium carrier: A reactor with a stirrer was equipped with a reflux condenser, a thermometer and a burette. After air in the reactor was fully replaced with nitrogen, ethanol and a small amount of isooctanol were added into the reactor, and elementary iodine and magnesium chloride were also added to be dissolved. Magnesium powder and toluene were then added. A titanate compound having a certain structure was added to a feed liquid of a reaction to carry out the reaction. After stirring, a temperature was increased to reach a reflux temperature of a reaction system. The reaction was carried out until the reaction was completed, i.e. no hydrogen was discharged. Then, washing, separating and drying were performed. Additions of respective raw materials and a result are shown in Table 1.

Preparation of a catalyst: A process is same as that in Example 1.

Propylene polymerization: A process is same as that in Example 1.

Specific data are shown in Table 1.

Comparative Example 3

Preparation of an alkoxymagnesium carrier: A process is same as that in Example 2 except that no tetrabutyl titanate was added in the preparation process. A result is shown in Table 1.

Preparation of a catalyst: A solid catalyst component was prepared by using alkoxymagnesium particle prepared. 10 mL of toluene and 90 mL of titanium tetrachloride were added into a 300 mL reactor after air therein was repeatedly replaced with high purity nitrogen. After a temperature was increased to 50° C., a suspension prepared with 10 g of the akoxymagnesium particle prepared, 50 mL of toluene, and 1.2 mL of a carboxylate ester (di-n-butyl phthalate DNBP is used for explanation, but the carboxylate ester is not limited to this compound) was added. The temperature was slowly increased, and when the temperature reached 80° C., 5 g of tetrabutyl titanate was added. The temperature was increased up to 115° C. and maintained for 2 h, and then liquid was removed by filtration under reduced pressure. Then a mixed solution of 30 mL of titanium tetrachloride and 120 mL of toluene was added. After the temperature was increased to 110° C., 1.5 mL of DNBP was added by dropping. After a stirring treatment is performed for 1 h, the liquid was removed by filtration under reduced pressure. Then, a mixed solution of 120 mL of titanium tetrachloride and 30 mL of toluene was added. The temperature was increased to 110° C., and a stirring treatment was performed for 1 h. Such treatment was repeated for 2 times, and the liquid is removed by filtration. An obtained solid was washed with 150 mL of hexane for 4 times at a temperature of 60° C., and the liquid was removed by filtration. After drying was performed, solid powder was obtained, which is the solid catalyst component. Specific data are shown in Table 1.

Propylene polymerization: A process is same as that in Example 1.

Specific data are shown in Table 1.

TABLE 1

Data of added materials and results for carriers and catalysts examples and comparative examples

| item | material | Example 1 | Example 2 | Example 3 | Example 4 | Example 5 | Example 6 | Example 7 | Example 8 |
|---|---|---|---|---|---|---|---|---|---|
| Raw materials for preparing a carrier | Magnesium powder [g] | 32 | 32 | 32 | 32 | 32 | 32 | 32 | 32 |
| | Ethanol [ml] | 260 | 260 | 380 | 260 | 260 | 380 | 260 | 260 |
| | Isooctanol [ml] | 10 | 20 | 10 | 20 | 10 | 10 | 20 | 10 |
| | Elementary iodine [g] | 1.6 | 1.6 | 2.0 | 1.6 | 1.6 | 2.0 | 1.6 | 1.6 |
| | Magnesium chloride [g] | 0.4 | 0.4 | 0.6 | 0.4 | 0.4 | 0.6 | 0.4 | 0.4 |
| | Titanate [g] | Tetrabutyl titanate 5.0 | Tetrabutyl titanate 0.5 | Tetrabutyl titanate 60 | Tetraethyl titanate 0.5 | Tetraethyl titanate 5.0 | Tetraethyl titanate 60 | Tetra-isopropyl titanate 0.5 | Tetra-isopropyl titanate 5.0 |
| | Toluene [ml] | 120 | 120 | 0 | 120 | 120 | 0 | 120 | 120 |
| Alkoxy-magnesium carrier | d50 [μm] | 33.5 | 32.2 | 37.6 | 31.2 | 32.1 | 36.5 | 33.3 | 35.9 |
| | Span | 0.82 | 0.70 | 0.80 | 0.82 | 0.81 | 0.96 | 0.72 | 0.88 |
| | BD [g/cm$^3$] | 0.45 | 0.42 | 0.46 | 0.40 | 0.44 | 0.45 | 0.40 | 0.43 |
| | Titanate content [wt %] | 1.1 | 0.2 | 5.5 | 0.5 | 1.7 | 6.8 | 0.3 | 1.5 |
| Catalyst | Titanate addition [g] | 0 | 0 | 0 | 0 | 0 | 0 | 0 | 0 |
| | Titanium content [wt %] | 2.6 | 2.5 | 3.2 | 2.7 | 2.9 | 3.5 | 2.6 | 2.8 |
| | Electron donor content [wt %] | DNBP 13.0 | DNBP 13.2 | DNBP 14.1 | DNBP 13.1 | DNBP 13.5 | DNBP 14.3 | DNBP 12.8 | DNBP 13.6 |
| | Activity [KgPP/gCat] | 77.8 | 76.5 | 71.1 | 75.5 | 76.9 | 70.8 | 72.2 | 73.5 |
| Polymer | BD [g/cm$^3$] | 0.43 | 0.41 | 0.44 | 0.41 | 0.42 | 0.43 | 0.41 | 0.42 |
| | MI [g/10 min] | 2.9 | 2.6 | 3.1 | 2.8 | 2.7 | 3.2 | 2.9 | 3.0 |
| | Fine powder [wt %] | 0.2 | 0.4 | 0.3 | 0.4 | 0.3 | 0.3 | 0.3 | 0.3 |
| | II [g/10 min] | 98.9 | 98.7 | 98.6 | 98.7 | 98.8 | 98.5 | 98.7 | 98.6 |

| item | material | Example 9 | Example 10 | Example 11 | Example 12 | Example 13 | Example 14 | Comparative Example 1 | Comparative Example 2 | Comparative Example 3 |
|---|---|---|---|---|---|---|---|---|---|---|
| Raw materials for preparing a carrier | Magnesium powder [g] | 32 | 32 | 32 | 32 | 32 | 32 | 32 | 32 | 32 |
| | Ethanol [ml] | 380 | 260 | 260 | 380 | 380 | 260 | 260 | 630 | 260 |
| | Isooctanol [ml] | 10 | 10 | 10 | 10 | 10 | 10 | 20 | 0 | 10 |
| | Elemetary iodine [g] | 2.0 | 1.6 | 1.6 | 2.0 | 2.0 | 2.5 | 1.6 | 1.0 | 1.6 |
| | Magnesium chloride [g] | 0.6 | 0.4 | 0.4 | 0.6 | 0.6 | 0.6 | 0.4 | 0 | 0.4 |

TABLE 1-continued

Data of added materials and results for carriers and catalysts examples and comparative examples

|  |  | | | | | | | | | |
|---|---|---|---|---|---|---|---|---|---|---|
|  | Titanate [g] | Tetra-isopropyl titanate 60 | Tetrabutyl titanate 5.0 | Tetrabutyl titanate 5.0 | Tetrabutyl titanate 90 | Tetrabutyl titanate 120 | Tetrabutyl titanate 160 | 0 | 0 | 0 |
|  | Toluene [ml] | 0 | 120 | 120 | 0 | 0 | 0 | 120 | 0 | 120 |
| Alkoxy-magnesium carrier | d50 [μm] | 39.8 | 33.5 | 33.5 | 55.7 | 66.8 | 88.6 | 33.3 | 8.4 | 31.2 |
|  | Span | 0.95 | 0.82 | 0.82 | 0.86 | 0.98 | 1.51 | 0.75 | 1.62 | 0.89 |
|  | BD[g/cm$^3$] | 0.44 | 0.45 | 0.45 | 0.46 | 0.46 | 0.47 | 0.36 | 0.28 | 0.35 |
|  | Titanate content [wt %] | 6.2 | 1.1 | 1.1 | 7.0 | 7.7 | 9.7 | 0 | 0 | 0 |
| Catalyst | Titanate addition [ml] | 0 | 0 | 0 | 0 | 0 | 0 | 0 | 0 | 5.0 |
|  | Titanium content [wt %] | 3.1 | 3.3 | 3.1 | 3.3 | 3.5 | 3.9 | 2.4 | 2.5 | 2.6 |
|  | Electron donor content [wt %] | DNBP 14.8 | JS 11.0 | 2#ester12.1 | DNBP 14.6 | DNBP 15.0 | DNBP 15.2 | DNBP 12.7 | DNBP 12.0 | DNBP 13.0 |
|  | Activity [KgPP/gCat] | 66.7 | 67.8 | 93.6 | 71.3 | 67.9 | 56.3 | 75.2 | 72.7 | 68.7 |
| Polymer | BD[g/cm$^3$] | 0.43 | 0.41 | 0.42 | 0.45 | 0.42 | 0.42 | 0.39 | 0.38 | 0.39 |
|  | MI [g/10 min] | 3.5 | 0.3 | 5.1 | 3.3 | 3.5 | 4.0 | 2.7 | 2.9 | 2.1 |
|  | Fine powder [wt %] | 0.5 | 0.3 | 0.5 | 0.2 | 0.5 | 1.1 | 0.4 | 1.5 | 0.5 |
|  | II [g/10 min] | 98.3 | 98.0 | 99.1 | 98.5 | 98.3 | 98.0 | 98.7 | 98.5 | 98.4 |

It can be seen from the data in Table 1 that alkoxymagnesium particle of the present invention have a more compact structure and a significantly improved bulk density; and when a mixed alcohol and a mixed halogenating agent are used, the alkoxymagnesium particle can have a good morphology and uniform distribution. When a propylene polymerization is carried out using a catalyst provided by the present invention, a bulk density of an obtained polymer can be remarkably improved, and the bulk density of the polymer can be increased by 10% or more under same conditions (e.g., Comparative Embodiment 1 and Embodiment 1). At the same time, polymerization activity is high, and polymer particle have a small content of fine powder and better fluidity, which is advantageous for long-term stable application of the catalyst on a large-scale propylene polymerization apparatus. The catalyst has broad application prospects.

The present disclosure is explained in combination with some embodiments hereinabove. However, various improvements can be made to the embodiments, and substances therein can be substituted by equivalents without departing from the protection scope of the present disclosure. Respective features disclosed in respective embodiments of the present disclosure can be combined with one another in any way, and no exhaustive description is made to the combinations only for saving space and resources. The present disclosure is not limited by the specific embodiments disclosed herein, but includes all technical solutions falling into the protection scope of the claims.

The invention claimed is:

1. An alkoxymagnesium particle, comprising a reaction product of a reaction mixture comprising reactants of 1) magnesium powder; 2) a mixed alcohol; 3) a halogenating agent; 4) a titanate compound; and optionally 5) a dispersing agent, wherein the alkoxymagnesium particle comprises titanium in an interior and on a surface thereof, the bulk density units should be changed from g/m$^3$ to g/cm$^3$ wherein a mass percentage of the titanate compound is 0.1-8.0 wt % of a total weight of the alkoxymagnesium particle, and wherein the dispersing agent is selected from hexane, heptane, octane, decane, benzene, toluene, xylene, and mixtures thereof.

2. The alkoxymagnesium particle according to claim 1, wherein the titanate compound has a structure of Formula I:

$$(R^1O)_a Ti(OR^2)_b (OR^3)_c X_d \quad \text{Formula I,}$$

wherein $R^1$, $R^2$ and $R^3$ are identical to or different from each other, and are independently H or an alkyl; X is selected from alkoxy, carboxyl, halogen, sulfonic acid group, phosphoric acid group, and sulfuric acid group; and each of a, b, c and d independently represents an integer number in a range of 0 to 4, and a+b+c+d=4.

3. The alkoxymagnesium particle according to claim 1, wherein the halogenating agent is an elementary halogen and/or an inorganic halide, and the mixed alcohol is a linear or branched monohydric alcohol or polyhydric alcohol.

4. The alkoxymagnesium particle according to claim 1, wherein a molar ratio of the halogenating agent to the magnesium powder measured by halogen atoms is (0.0002-0.2):1 and a molar ratio of the mixed alcohol to the magnesium powder is (2-50):1.

5. The alkoxymagnesium particle according to claim 1, wherein the mixed alcohol is a mixture of ethanol and isooctanol and the halogenating agent is a mixture iodine and magnesium chloride.

6. The alkoxymagnesium particle according to claim 5, wherein a molar ratio between the dispersion agent and the titanate compound is the reaction mixture used is 1.3 mol to 1.45 mmol to 1.3 mol to 17.6 mmol.

7. An alkoxymagnesium particle, comprising a titanate compound in the particle, wherein the titanate compound is distributed from an interior and to a surface of the alkoxymagnesium particle and has a bulk density in a range of 0.40 g/cm³ to 0.47 g/cm³, and a mass percentage of the titanate compound is 0.1-8.0 wt % of a total weight of the alkoxymagnesium particle.

8. The alkoxymagnesium particle according to claim 7, wherein the titanate compound has a structure as shown in formula I:

Formula I, wherein, $R^1$, $R^2$ and $R^3$ are identical to or different from each other, and are independently selected from a group consisting of H and alkyl; X is selected from a group consisting of alkoxy, carboxyl, halogen, sulfonic acid group, phosphoric acid group, and sulfuric acid group; and each of a, b, c and d independently represents an integer number in a range of 0 to 4, and a+b+c+d=4.

9. The alkoxymagnesium particle according to claim 7, wherein a method for preparing the alkoxymagnesium particle comprises: providing a reaction mixture comprising reactants of 1) a magnesium powder, 2) a mixed alcohol, 3) a halogenating agent, and 4) the titanate compound, and carrying out a reaction in the reaction mixture to form the alkoxymagnesium particle.

10. The alkoxymagnesium particle according to claim 9, wherein a weight ratio of the titanate compound to the magnesium powder is (0.01-5):1.

11. The alkoxymagnesium particle according to claim 9, wherein a molar ratio of the halogenating agent to the magnesium powder measured by halogen atoms is (0.0002-0.2):1.

12. The alkoxymagnesium particle according to claim 9, wherein the reaction mixture further comprises a dispersing agent, and the dispersing agent is an inert organic solvent.

13. A Ziegler-Natta catalyst component, comprising a reaction product of the alkoxymagnesium particle of claim 1, a titanium-containing halide, and an electron donor compound.

14. The catalyst component according to claim 13, wherein the electron donor compound is selected from a carboxylate compound, a 2,3-di-non-linear alkyl-2-cyano disuccinate compound, an aliphatic ether compound, and mixtures thereof, wherein the carboxylate compound is a mono benzoate compound or a phthalate compound as shown in Formula II Formula II wherein, in Formula II, $R_1$ and $R_2$ are identical to or different from each other, and are independently selected from the group consisting of substituted or unsubstituted $C_1$-$C_8$ alkyl, $C_3$-$C_{10}$ cycloalkyl or $C_6$-$C_{20}$ aryl; $R_3$-$R_6$ are independently selected from the group consisting of hydrogen, halogen, $C_1$-$C_4$ alkyl, and $C_1$-$C_4$ alkoxy, and/or, the 2,3-di-non-linear alkyl-2-cyano disuccinate compound has a structure of Formula III:

Formula III wherein, $R_1$ and $R_2$ are identical to or different from each other, and each is a linear alky of 1 to 10 carbon atoms, a branched alkyl or cycloalkyl of 3 to 10 carbon atoms, an aryl of 6 to 10 carbon atoms, an alkaryl or aralkyl of 7 to 10 carbon atoms, wherein a hydrogen atom on a carbon in said alkyl, cycloalkyl, aryl, alkaryl or aralkyl is unsubstituted or substituted by a halogen (hetero) atom, alkyl, or alkoxy, and a carbon atom on a main chain is unsubstituted or substituted by a hetero atom; and/or, wherein the aliphatic ether compound is at least one selected from the group consisting of: 2,2'-di-n-propyl-1,3-dimethyl ether, 2,2'-diisopropyl-1,3-dimethyl ether, 2,2'-di-n-butyl-1,3-dimethyl ether, 2,2'-diisobutyl-1,3-dimethyl ether, 2,2'-di-n-pentyl-1,3-dimethyl ether, 2,2'-diisopentyl-1,3-dimethyl ether, 2,2'-di-n-hexyl-1,3-dimethyl ether, 2,2'-diisohexyl-1,3-diether, 2-n-propyl-2-isopropyl-1,3-dimethyl ether, 2-n-propyl-2-n-butyl-1,3-dimethyl ether, 2-n-propyl-2-isobutyl-1,3-dimethyl ether, 2-n-propyl-2-n-pentyl-1,3-dimethyl ether, 2-n-propyl-2-isopentyl-1,3-dimethyl ether, 2-n-propyl-2-n-hexyl-1,3-dimethyl ether, 2-n-propyl-2-isohexyl-1,3-dimethyl ether, 2-isopropyl-2-n-butyl-1,3-dimethyl ether, 2-isopropyl-2-isobutyl-1,3-dimethyl ether, 2-isopropyl-2-n-pentyl-1,3-dimethyl ether, 2-isopropyl-2-isopentyl-1,3-dimethyl ether, 2-isopropyl-2-n-hexyl-1,3-dimethyl ether, 2-isopropyl-2-isohexyl-1,3-dimethyl ether, 2-n-butyl-2-isobutyl-1,3-dimethyl ether, 2-n-butyl-2-n-pentyl-1,3-dimethyl ether, 2-n-butyl-2-isopentyl-1,3-dimethyl ether, 2-n-butyl-2-n-hexyl-1,3-dimethyl ether, 2-n-butyl-2-isohexyl-1,3-dimethyl ether, 2-isobutyl-2-n-pentyl-1,3-dimethyl ether, 2-isobutyl-2-isopentyl-1,3-dimethyl ether, 2-isobutyl-2-n-hexyl-1,3-dimethyl ether, 2-isobutyl-2-isohexyl-1,3-dimethyl ether, 2-n-pentyl-2-isopentyl-1,3-dimethyl ether, 2-n-pentyl-2-n-hexyl-1,3-dimethyl ether, 2-n-pentyl-2-isohexyl-1,3-dimethyl ether, 2-isopentyl-2-n-hexyl-1,3-dimethyl ether, 2-isopentyl-2-isohexyl-1,3-dimethyl ether, and 2-n-hexyl-2-isohexyl-1,3-dimethyl ether and/or, the titanium-containing halide is of Formula IV:

Formula IV wherein, in Formula IV, X is halogen; $R_7$ is $C_1$-$C_{20}$ alkyl; and n is an integer number in a range of 0-4.

15. A catalyst for olefin polymerization, comprising a reaction product of the following components:

(1) the catalyst component according to claim 13;
(2) an organic aluminum compound; and
(3) optionally, an external electron donor compound.

16. The catalyst according to claim 15, wherein the organic aluminum compound is an organic aluminum compound of Formula $AlR'_m X'_{3-m}$, wherein R' is at least one selected from hydrogen, $C_1$-$C_{20}$ alkyl, and $C_6$-$C_{20}$ aryl; X' is halogen; and m is an integer number in a range of 1-3; and/or the external electron donor compound is an organic silicon compound of $R^4{}_p R^5{}_q Si(OR^6)_{4-p-q}$, wherein $R^4$ and $R^5$ are independently at least one selected from halogen, hydrogen atom, $C_1$-$C_{20}$ alkyl, $C_3$-$C_{20}$ cycloalkyl, $C_6$-$C_{20}$ aryl, and $C_1$-$C_{20}$ haloalkyl; $R^6$ is selected from $C_1$-$C_{20}$ alkyl, $C_3$-$C_{20}$ cycloalkyl, $C_6$-$C_{20}$ aryl, and $C_1$-$C_{20}$ haloalkyl; and p and q respectively are an integer number in a range of 0-3, and p+q<4.

17. The catalyst according to claim 15, wherein a molar ratio of aluminum in the organic aluminum compound to titanium in the catalyst component is (5-5000):1, and/or a molar ratio of aluminum in the organic aluminum compound to the external electron donor compound is (0.1-500):1.

18. A method of olefin polymerization, comprising contacting olefin with the catalyst according to claim 15 under olefin polymerization conditions, wherein at least one of the olefin is represented by formula $CH_2=CHR$, in which R is one of hydrogen and $C_1$-$C_6$ alkyl.

19. The alkoxymagnesium particle according to claim 1, wherein the titanate compound is at least one selected from tetramethyl titanate, tetraethyl titanate, tetra-n-propyl titanate, tetra-n-butyl titanate, tetra-n-pentyl titanate, tetra-n-hexyl titanate, tetra-n-heptyl titanate, tetra-isooctyl titanate, tetra-n-nonyl titanate, tetra-n-decyl titanate, and isomers thereof.

20. The alkoxymagnesium particle according to claim 5, wherein the reaction is carried out at a temperature from 0° C. to a reflux temperature of the reaction mixture for 2-30 h to obtain the alkoxymagnesium particle.

21. The alkoxymagnesium particle according to claim 7, wherein the titanate compound selected from tetramethyl titanate, tetraethyl titanate, tetra-n-propyl titanate, tetra-n-butyl titanate, tetra-n-pentyl titanate, tetra-n-hexyl titanate, tetra-n-heptyl titanate, tetra-isooctyl titanate, tetra-n-nonyl titanate, tetra-n-decyl titanate, and isomers thereof.

22. The alkoxymagnesium particle according to claim 9, wherein a reaction temperature of the reaction is in a range from 0° C. to a reflux temperature of the reaction mixture for 2-30 h.

23. The catalyst component according to claim 13, wherein an amount of the electron donor compound is 0.005-10 mol relative to an amount of magnesium in 1 mol of a dialkoxymagnesium compound; and/or an amount of the titanium-containing halide is 0.5-100 mol.

24. The catalyst component according to claim 14, wherein:

the carboxylate compound is at least one selected from di-n-butyl phthalate, diisobutyl phthalate, diethyl phthalate, dipentyl phthalate, dioctyl phthalate, methyl benzoate, ethyl benzoate, propyl benzoate, isopropyl benzoate, butyl benzoate and isobutyl benzoate; and/or, the 2,3-di-non-linear alkyl-2-cyano disuccinate compound is at least one selected from diethyl 2,3-diisopropyl-2-dicyano succinate, diethyl 2-cyano-2,3-diisopropyl succinate, diethyl 2-cyano-2,3-di-n-butyl succinate, diethyl 2-cyano-2,3-diisobutyl succinate, diethyl 2-cyano-2,3-di-n-pentyl succinate, diethyl 2-cyano-2,3-diisopentyl succinate, diethyl 2-cyano-2-isopropyl-3-n-butyl succinate, diethyl 2-cyano-2-isopropyl-3-isobutyl succinate, diethyl 2-cyano-2-isopropyl-3-n-pentyl succinate, diethyl 2-cyano-2-isopropyl-3-isopentyl succinate, diethyl 2-cyano-2-isopropyl-3-cyclopentyl succinate, diethyl 2-cyano-2-n-butyl-3-isopropyl succinate, diethyl 2-cyano-2-isobutyl-3-isopropyl succinate, diethyl 2-cyano-2-n-pentyl-3-isopropyl succinate, diethyl 2-cyano-2-isopentyl-3-isopropyl succinate, and diethyl 2-cyano-2-cyclopentyl-3-isopropyl succinate; and/or, the aliphatic ether compound is at least one selected from 2-isopropyl-2-(3-methyl butyl)-1,3-dimethoxy propane, 2,2'-diisopropyl-1,3-dimethyl ether, 2,2'-diisobutyl-1,3-dimethyl ether, 2,2'-diisopentyl-1,3-dimethyl ether, 2-isopropyl-2-isobutyl-1,3-dimethyl ether, 2-isopropyl-2-n-pentyl-1,3-dimethyl ether, 2-isopropyl-2-isopentyl-1,3-dimethyl ether, 2-isopropyl-2-isohexyl-1,3-dimethyl ether, 2-isobutyl-2-n-pentyl-1,3-dimethyl ether, 2-isobutyl-2-isopentyl-1,3-dimethyl ether, and 2-n-pentyl-2-isopentyl-1,3-dimethyl ether.

25. The method of olefin polymerization according to claim 18, wherein the olefin polymerization is carried out at a temperature of 0-150° C. for a time duration of 0.1-5 h and under a pressure of 0.01-10 MPa.

\* \* \* \* \*

UNITED STATES PATENT AND TRADEMARK OFFICE
CERTIFICATE OF CORRECTION

| | |
|---|---|
| PATENT NO. | : 11,332,425 B2 |
| APPLICATION NO. | : 16/345596 |
| DATED | : May 17, 2022 |
| INVENTOR(S) | : Xiudong Xu et al. |

It is certified that error appears in the above-identified patent and that said Letters Patent is hereby corrected as shown below:

In the Claims

Claim 1 reading:
-1. An alkoxymagnesium particle, comprising a reaction product of a reaction mixture comprising reactants of 1) magnesium powder; 2) a mixed alcohol; 3) a halogenating agent; 4) a titanate compound; and optionally 5) a dispersing agent, wherein the alkoxymagnesium particle comprises titanium in an interior and on a surface thereof, the bulk density units should be changed from $g/m^3$ to $g/cm^3$ wherein a mass percentage of the titanate compound is 0.1-8.0 wt% of a total weight of the alkoxymagnesium particle, and wherein the dispersing agent is selected from hexane, heptane, octane, decane, benzene, toluene, xylene, and mixtures thereof.-

Should be changed to:
-1. An alkoxymagnesium particle, comprising a reaction product of a reaction mixture comprising reactants of 1) magnesium powder; 2) a mixed alcohol; 3) a halogenating agent; 4) a titanate compound; and optionally 5) a dispersing agent, wherein the alkoxymagnesium particle comprises titanium in an interior and on a surface thereof, the bulk density in a range of 0.40 $g/cm^3$ to 0.47 $g/cm^3$, wherein a mass percentage of the titanate compound is 0.1-8.0 wt% of a total weight of the alkoxymagnesium particle, and wherein the dispersing agent is selected from hexane, heptane, octane, decane, benzene, toluene, xylene, and mixtures thereof.-

Signed and Sealed this
Eighth Day of August, 2023

*Katherine Kelly Vidal*

Katherine Kelly Vidal
*Director of the United States Patent and Trademark Office*